United States Patent [19]

Vanlerberghe et al.

[11] 4,172,887

[45] Oct. 30, 1979

[54] HAIR CONDITIONING COMPOSITIONS CONTAINING CROSSLINKED POLYAMINOPOLYAMIDES

[75] Inventors: Guy Vanlerberghe, Commune de Villevaude; Henri Sebag, Paris; Jean-François Grollier, Paris; Alexandre Zysman, Paris, all of France

[73] Assignee: L'Oreal, Paris, France

[21] Appl. No.: 762,804

[22] Filed: Jan. 26, 1977

Related U.S. Application Data

[63] Continuation of Ser. No. 528,577, Nov. 29, 1974, abandoned.

[30] Foreign Application Priority Data

Nov. 30, 1973 [LU] Luxembourg ............................ 68901

[51] Int. Cl.$^2$ ........................ A61K 7/06; A61K 7/08; A61K 7/09; A61K 7/11
[52] U.S. Cl. ........................................ 424/70; 525/435; 8/127.51; 252/DIG. 2; 252/DIG. 3; 252/DIG. 13; 260/29.2 EP; 260/29.2 UA; 260/29.6 T; 260/29.6 TA; 260/29.6 BE; 260/29.6 HN; 424/DIG. 2; 424/71; 424/78; 424/81
[58] Field of Search ........................ 424/70, 71, 78, 81, 424/DIG. 2; 260/785 C, 29.2 EP, 29.2 UA, 29.6 T, 29.6 TA, 29.6 BE, 29.6 HN; 252/DIG. 2, DIG. 3, DIG. 13; 8/127.51

[56] References Cited

U.S. PATENT DOCUMENTS

| | | | |
|---|---|---|---|
| 2,882,185 | 4/1959 | Valko et al. | 260/785 C X |
| 2,926,116 | 2/1960 | Keim | 260/785 C X |
| 2,926,154 | 2/1960 | Keim | 260/785 C X |
| 3,560,609 | 2/1971 | Korden | 424/71 |
| 3,560,610 | 2/1971 | Korden | 424/71 |
| 3,769,398 | 10/1973 | Hewitt | 424/70 |

FOREIGN PATENT DOCUMENTS 1035296 7/1966 United Kingdom ...................... 424/71

*Primary Examiner*—James O. Thomas, Jr.
*Assistant Examiner*—Vera C. Clarke
*Attorney, Agent, or Firm*—Cushman, Darby & Cushman

[57] ABSTRACT

A cosmetic composition for the hair comprises at least one water-soluble crosslinked polymer selected from the group consisting of (1) crosslinked polymer obtained by crosslinking a polyamino-polyamide with a crosslinking agent, said polyamino-polyamide being prepared by the polycondensation of (a) an acidic compound selected from the group consisting of (i) organic dicarboxylic acid, (ii) ethylenically unsaturated aliphatic mono- or di- carboxylic acid, (iii) ester of said acids of (i) and (ii), and (iv) mixtures of (i), (ii) and (iii) on (b) a polyamine selected from the group consisting of bis primary and mono- or bis-secondary polyalkylene polyamines, said polyamine (b) being replaceable by a member selected from the group consisting of (1) 0–20 mole percent hexamethylene diamine, (2) 0–40 mole percent bis-primary amine and (3) 0–40 mole percent bis-secondary amine, said crosslinking agent being selected from the group consisting of epihalohydrins, diepoxides, dianhydrides and bis unsaturated derivatives, and being employed in amounts of 0.025–0.35 mole per amine group in said polyamino-polyamide and (2) the crosslinked polymer of (1) alkylated with an alkylating agent selected from the group consisting of (a) epoxides, (b) ethylenically unsaturated compounds, (c) chloroacetic acid, and (d) alkane sultone selected from the group consisting of propane sultone and butane sultone. The said crosslinked polymer is soluble in water in amounts of 10 weight percent thereof without essentially any gel formation and a 10 weight percent aqueous solution of the said crosslinked polymer has a viscosity greater than 3 centipoises at 25° C.

25 Claims, No Drawings

HAIR CONDITIONING COMPOSITIONS CONTAINING CROSSLINKED POLYAMINOPOLYAMIDES

This is a continuation of application Ser. No. 528,577 filed Nov. 29, 1974, now abandoned.

The present invention relates to a cosmetic composition for improving the condition of hair as well as its appearance.

It is known that the hair of many people, because of its general condition or because of repeated exposure to the atmosphere or to treatments such as bleachings, permanent wavings or dyeings, becomes degraded and often difficult to comb out or to set, especially in the case of a thick head of hair which is often dry, dull, rough or lacks vigor and liveliness.

Efforts heretofore have been made to limit or to correct these faults by applying to the hair a "hair conditioner" composition so as to improve the condition of moist and dry hair and to facilitate such operations as combing and setting the hair.

By "hair conditioning" is meant an operation which, while facilitating the combing out of moist hair, also imparts to dry hair some swelling and elasticity, so as to assure good maintenance of the coiffure or style imparted thereto. The agents employed to achieve such "hair conditioning" are generally called "hair conditioners".

Conventionally there is employed in the conditioning of hair various synthetic polymers, such as polyethylene imines, polyvinylpyridines, the polychloride of p-vinylbenzyl trimethylammonium and the polychloride of diallyl dimethyl ammonium. However, it has also been found that these polymers suffer from the disadvantage of not being compatible with, for instance, anionic shampoo compositions.

It has also been known to use in the production of compositions for hair some polyamino-amide polymers, obtained by the polycondensation of a dicarboxylic acid and a polyalkylene polyamine, some polyaminoureylene polymers and some alkylene polyamine polymers modified particularly by epichlorohydrin in quantities near stoichiometric amounts relative to the amine groups of the polyamino-amide. However, the addition of these significant quantities of epichlorohydrin leads to the presence in the molecules of the crosslinked polymer some reactive groups. These polymers thus contain alkylating groups which are capable of reacting on nucleophilic groups such as amines, thiols, sulfates and the like. Representative of such alkylating groups are azetidinium rings. However, as a result of the presence of such reactive groups, the polymer lacks stability and generally degrades when put into solution. Further the presence of such alkylating groups renders cosmetic products incorporating the same of doubtful use for application to human skin.

There has also been recommended the use in a "hair conditioner" composition of heat crosslinkable thermosetting polymers, but their use necessarily involves a special heating step.

The present invention, in contrast, relates to a hair conditioner which avoids these drawbacks and which comprises a chemically stable, crosslinked polyaminopolyamide free from reactive groups.

The present invention also relates to a hair conditioning composition in a form ready to use which can be applied to living human hair at ambient temperature.

The present invention also relates to a hair conditioner which is (1) compatible with anionic shampoo compositions, (2) assures satisfactory combing out of moist hair, and (3) imparts good elasticity to dry hair so as to assure good maintenance of the coiffure or style imparted to the hair.

The present invention also relates to a hair conditioning cosmetic composition comprising at least one water-soluble crosslinked polymer obtained by crosslinking a polyamino-polyamide which in turn is prepared by the polycondensation of an acidic compound on a polyamine. The acidic compound is selected from the group consisting of:
(i) an organic dicarboxylic acid,
(ii) an ethylenically unsaturated aliphatic mono- or dicarboxylic acid,
(iii) an ester of said acids, preferably with a lower alkanol having from 1–6 carbon atoms, and
(iv) mixtures of these compounds.

The polyamine usefully employed to produce the polyaminopolyamide is selected from the group consisting of bis primary and mono- or bis- secondary polyalkylene-polyamines. 0–40 mole percent of the selected polyamine can be replaced by a bis-primary amine, preferably, ethylenediamine or by a bis-secondary amine, preferably piperazine and 0–20 mole percent of the selected polyamine can be replaced by hexamethylene-diamine.

Crosslinking of the polyamino-polyamide is effected with a crosslinking agent selected from the group consisting of epihalohydrins, diepoxides, dianhydrides, unsaturated anhydrides and the bis unsaturated derivatives, and is characterized by the fact that the crosslinking agent is employed in amounts of 0.025–0.35 mole of crosslinking agent per amine group of the polyaminopolyamide and generally from 0.025 up to about 0.2 mole and, in particular, from 0.025 to up to about 0.1 mole of crosslinking agent per amine group of the polyamino-polyamide.

The crosslinked polyamino-polyamide present in the hair conditioning composition of the present invention exhibits the following characteristics: (1) it is perfectly soluble in water up to 10 weight percent concentration without forming a gel; (2) the viscosity of such a 10% solution in water at 25° C. is greater than 3 centipoises, the viscosity generally measuring between 3–200. More often the viscosity of such a solution is equal to or greater than 20 centipoises and lower than 50 centipoises; (3) the polyamino-polyamide does not carry any reactive group and in particular it is chemically stable and does not have any alkylating characteristics.

Representative specific acids usefully employed in the production of the polyamino-polyamides of the present invention are selected from the group consisting of saturated aliphatic dicarboxylic acids having from 6 to 10 carbon atoms, for example adipic acid, 2,2,4-trimethyl and 2,4,4-trimethyl adipic acids; aromatic dicarboxylic acids such as terephthalic acid; and ethylenically unsaturated aliphatic mono- and di- carboxylic acids such as acrylic acid, methacrylic acid and itaconic acid.

Adipic acid is particularly preferred.

The esters of the above mentioned acids can also usefully be employed as can mixtures of two or more of said carboxylic acids or their esters.

Representative specific polyamines usefully employed in the preparation of the polyamino-polyamides of the present invention are selected from the group consisting of the bis primary and mono- or bis-secondary polyalkylene-polyamines, such as diethylene triamine, dipropylene triamine, triethylene tetraamine and their mixtures.

The polycondensation reaction is carried out in accordance with known procedures, by mixing the initial reactants; heating the resulting mixture to a temperature between about 80°–250° C., and preferably between about 100°–180° C., for 1–8 hours. The choice of the exact reaction time and temperature can depend on the choice of the particular initial reactants selected but the same is easily determined by those skilled in the art. After heating the reaction mixture according to the above schedule, the same is then subjected to total reflux for about 0.5–1 hour so as to eliminate the water or alcohol formed during the course of the polycondensation. Reflux is initially carried out at atmospheric pressure and then at sub-atmospheric pressure. The polycondensation reaction is also generally carried out under a nitrogen atmosphere to avoid any significant colorations and to facilitate the elimination of volatile substances.

In carrying out the polycondensation reaction, the dicarboxylic acid is preferably employed in equimolar proportions relative to the primary amine groups of the polyalkylene-polyamines. According to a preferred embodiment of the present invention, the polycondensation of the polyalkylene-polyamine selected preferably from the group of diethylene triamine, triethylene tetramine, dipropylene triamine and mixtures thereof is effected with either (1) a carboxylic diacid, preferably adipic acid or dimethyl ester, or (ii) the intermediate product of addition of one molecule of ethylenediamine and two molecules of the methyl ester of an ethylenically unsaturated acid such as methyl acrylate, methyl methacrylate or methyl itaconate.

The addition reaction of ethylenediamine on the said unsaturated ester is carried out by mixing the reactants at a temperature between 5°–80° C. The polycondensation reaction is effected by heating the reactants for 30–60 minutes at reflux followed by eliminating the methyl alcohol formed, at a temperature of 120°–150° C., or of the water formed at a temperature of 140°–175° C., initially under atmospheric pressure and finally under sub-atmospheric pressure of 15 mm of mercury. The polyamino-polyamides thus obtained have a viscosity in a 10% aqueous solution at 25° C. lower than 3 centipoises.

The preferred polyamino-polyamides of the present invention are characterized by repeating units of the formula $$\text{\textemdash}[OC\text{\textemdash}R\text{\textemdash}CO\text{\textemdash}Z]\text{\textemdash} \qquad (I)$$

wherein R represents a bivalent radical which is derived from the acid or from the addition product of the acid with a bis- primary or bis- secondary amine employed during the polycondensation reaction.

Representative preferred values for R include

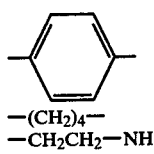
(1)

—(CH$_2$)$_4$— (2)

—CH$_2$CH$_2$—NH—CH$_2$—CH$_2$—NH—CH$_2$CH$_2$—, (3)

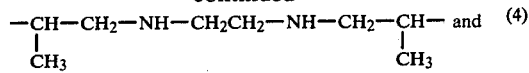

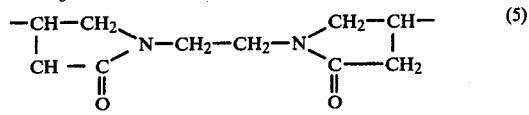

These radicals are derived, respectively, from terephthalic acid, adipic acid, the product of addition of ethylenediamine with acrylic acid, methacrylic acid and itaconic acid, or their esters;

Z is selected from the group consisting of:
(1) in amounts of 60–100 mole percent, the radical $$-NH\{(CH_2)_x-NH\}_n \qquad (II)$$

wherein (a) x=2 and n=2 or 3 or (b) x=3 and n=2, this radical being derived from diethylene triamine, triethylene tetramine or dipropylene triamine;

(2) in amounts of 0–40 mole percent (a) the radical (II) above, in which x=2 and n=1, the said radical being derived from ethylenediamine, or (b) the radical

deriving from piperazine; and (3) in amounts of 0–20 mole percent the radical —NH—(CH$_2$)$_6$—NH— which is derived from hexamethylenediamine.

The polyamino-polyamides thus obtained are then crosslinked by the addition of a crosslinking agent. As the crosslinking agent there is employed a bifunctional compound selected from the group consisting of (a) epihalohydrins, for example epichlorohydrin; (b) diepoxides, such as diglycidyl ether, N,N'-bis epoxy propyl piperazine; (c) dianhydrides, for example the dianhydride of butane tetracarboxylic acid and the dianhydride of pyromellitic acid; and (d) bis unsaturated derivatives, for example divinylsulfone and methylene bisacrylamide.

An advantageously useful crosslinking agent is epichlorohydrin. Other preferred crosslinking agents are divinylsulfone, methylene bisacrylamide, diglycidyl ether and N,N'-bis epoxy propyl piperazine.

These crosslinking agents provide, respectively, in the crosslinked polyamino-polyamide, the following radicals:

—CH$_2$—CHOH—CH$_2$—,

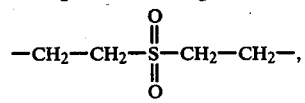

—CH$_2$—CH$_2$—CONH—CH$_2$—NHCO—CH$_2$—CH$_2$—,

—CH$_2$—CHOH—CH$_2$—O—CH$_2$—CHOH—CH$_2$— and

The crosslinking reaction is carried out by heating to a temperature of between about 20°–90° C. a 20–30 weight percent aqueous solution of the polyaminopolyamide to which has been added the said crosslinking agent in very small portions. The addition of the crosslinking agent is continued until there is observed a significant increase in the viscosity of the reaction mass without, however, there being formed a gel which would no longer be soluble in water. At this point the solids concentration of the reaction medium is then rapidly adjusted to 10% by the addition of water thereto. The reaction mixture is then cooled.

According to an essential characteristic of the present invention, the crosslinking agent for polyamino-polyamide polymers is employed in amounts of 0.025 to 0.35 mole per amine group of the polyamino-polyamide. An interesting category of crosslinked polymers is obtained by using from 0.025 to up to about 0.2 mole of crosslinking agent per amine group of the polyamino-polyamide. Another advantageous category of crosslinked polymers is obtained by using from 0.025 to up to about 0.1 mole of crosslinking agent per amine group of the polyamino-polyamide.

The amount of crosslinking agent to use, which can vary according to the nature of the polyamino-polyamide and of the crosslinking agent selected can be easily determined by adding the desired crosslinking agent to an aqueous solution of the polyamino-polyamide until the viscosity of a 10% solution is at 25° C. between 3 centipoises and the gel state while preserving its solubility in water.

Exceeding the above indicated amounts of the crosslinking agent causes the formation of a gel which is not water soluble due to excessive crosslinking. However, by increasing again the quantity of crosslinking agent there are obtained some polymers which are soluble in water but they exhibit an evolutionary character as a function of time and temperature. This evolutionary character is due to the presence in the crosslinked polymer of reactive substituents, vis-a-vis the nucleophilic group. When epichlorohydrin is employed as the crosslinking agent, in amounts approaching stoichiometric proportions, the reactive substituents are constituted principally by the azetidinium ring:

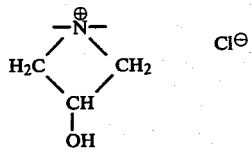

Known crosslinked polyamino-polyamide polymers which are utilized in compositions for the hair include reactive groups and consequently have poor stability characteristics.

However, the crosslinked polyamino-polyamides of the present invention are chemically stable, are compatible with anionic surface active agents and provide good combing out characteristics with moist hair. This compatibility with anionic surfactants can further be improved by alkylating the secondary amine group of the crosslinked polyamino-polyamides, in the presence of anionic surfactants.

Representative alkylating agents that can be employed include:

(1) an epoxide such as glycidol, ethylene oxide and propylene oxide;

(2) an ethylenically unsaturated compound such as acrylamide and acrylic acid;

(3) chloroacetic acid; and (4) an alkane sultone such as propane sultone or butane sultone.

The alkylation reaction can be carried out in aqueous solution containing 10-30 weight percent of said crosslinked polyamino-polyamide at a temperature between 10°-95° C. The proportion of alkylation agent relative to the total basicity, i.e. the number of moles of alkylating agent fixed relative to the total number of amine groups of the polyamino-polyamide varies from 0-80 percent. The basicity index of the polymer expressed in meq/g indicates the total number of milliequivalents of basic nitrogen per gram.

The crosslinked polymers according to the present invention can be used in various cosmetic compositions for the hair, for the treatment of normal hair and more particularly for sensitized hair. They can also be used in amounts of 0.1-5 percent, preferably from 0.2-2.5% and advantageously from 0.3-1.3 percent in cosmetic compositions for the hair and more particularly in shampoo compositions such as anionic, cationic, nonionic, amphoteric or zwitterionic shampoo formulations shampoo-dye compositions, dyes, hair dressing gels, hair dressing lotions, brushing lotions, hair setting lotions, hair rinse lotions, non-rinse reinforcing hair setting lotions, in hair restructuring compositions, and in antipellicular and antiseborrheic cosmetic compositions for the hair.

By a rinse lotion is meant a lotion that is applied after shampooing to obtain a hair conditioning effect, which lotion is rinsed from the hair after a short contact time therewith.

By a "brushing lotion" or a hair styling lotion is meant a lotion which is applied after shampooing and which improves the styling of the hair which is effected on damp or moist hair with the aid of a brush, during the drying of the hair with the aid of a hand dryer. This technique is suitable for relatively short hair.

By a non-rinse wave setting lotion is meant a lotion which is applied after shampooing and before setting and which is not rinsed from the hair. This lotion facilitates setting the hair, improves the style or coiffure imparted thereto and improves the durability of the style.

By structuring lotion is meant a lotion which contains components which reinforce the keratinic chain of the hair. Representative of such components are the methylol derivatives such as those described in French Pats. No. 1,527,085 and No. 1,519,979. These structuring agents are generally utilized in combination with cationic compounds which facilitate combing out the hair in a wet state.

The cosmetic compositions for hair containing a crosslinked polymer according to the present invention can have a pH between 2 and 11 and preferably between 3 and 8.

They can be provided under various conventional forms, i.e. as aqueous or hydroalcoholic solutions, gels, creams, dispersions or in the form of aerosols.

The cosmetic composition of the present invention can contain, in addition to the crosslinked polyamino-polyamide, components conventionally utilized in compositions for the hair such as anionic, cationic, nonionic, amphoteric or zwitterionic surface active agents, synergists, stabilizers, thickeners, emulsifying agents, softeners, preservatives, dyes, perfumes and the like. These compositions can also include other cosmetic resins, particularly nonionic, cationic or anionic resins.

The combination of the hair conditioners of the present invention with nonionic surface active agents provides a particularly interesting shampoo composition which is notable for imparting easy combing out characteristics to the hair.

Representative preferred cosmetic polymers or resins usefully employed in combination with the crosslinked polyamino-polyamide of the present invention include copolymers of 10% crotonic acid—90% vinyl acetate having a molecular weight of 10,000–70,000; copolymer of vinylpyrrolidone and vinyl acetate having a molecular weight of 30,000–360,000, the ratio of VP:VA being between 30:70 and 70:30; quaternary copolymers of vinylpyrrolidone having a molecular weight of about 1,000,000 such as that sold under the mark "GAF-QUAT 755", cationic polymers resulting from the condensation of piperazine or its derivatives (1) on bifunctional compounds such as alkyl dihalides or alkylaryl dihalides, bis-epoxides, epihalohydrins and bis unsaturated derivatives and/or (2) on a primary amine whose two hydrogen atoms can be substituted and which behaves as a bifunctional compound and (3) both on an epihalohydrin and on a hydroxylated amine such as diglycolamine, 2-amino-2-methyl-1,3-propanediol or on an amino acid such as glycocoll. Such cosmetic resins are generally employed in amounts of about 0.1 to 5 percent by weight of the cosmetic composition.

Representative surface active agents usefully employed in combination with the crosslinked polyamino-polyamide of this invention include (a) anionic surface active agents such as alkaline or alkanolamine salts of alkane sulfonates, alkyl sulfates and alkylether sulfates and their condensation products with ethylene oxide, for example, sodium or triethanolamine lauryl or myristyl ether sulfate and the disodium sulfosuccinate semi-ester of alkanolamides; (b) nonionic surface active agents such as (i) the condensation product of a monoalcohol, an $\alpha$-diol or an alkyl phenol with glycidol, for example, compounds of the formula $R-CHOH-CH_2-O-[CH_2-CHOH-CH_2-O]_nH$ wherein R represents an aliphatic, cycloaliphatic or arylaliphatic radical having from 7–21 carbon atoms and their mixtures, the aliphatic chains being able to carry ether, thioether and hydroxymethylene groups and $1 \leq n \leq 10$; (ii) compounds of the formula $RO-[C_2H_3O(CH_2OH)]_nH$ wherein R represents alkyl, alkenyl or alkylaryl and n is 10; (c) cationic surface active agents such as (i) dimethyl hydroxymethyl cetyl ammonium chloride or (ii) tetradecyl trimethylammonium bromide; and (d) amphoteric surface active agents such as the carboxylic derivatives of imidazole. These surface active agents are generally present in amounts of about 1 to 35 percent by weight of the cosmetic composition.

The cosmetic hair compositions of the present invention should be applied to sensitized hair in the presence of an electrolyte so as to reduce or suppress the tendency of the polyamino-polyamide to fix durably on the hair. Representative electrolytes include the alkali or alkaline earth salts of mineral or organic acids which are soluble in water. Preferably the electrolytes are the chlorides and acetates of sodium, potassium, ammonium and calcium. While the quantity of electrolyte is not critical, it is generally employed in amounts of about 0.01–5 weight percent and advantageously from about 0.4 to 3 percent by weight of the total cosmetic composition. The ratio electrolyte:polymer is between 0:1 and 1.5:1.

The polyamino-polyamide polymers crosslinked with the above indicated crosslinking agents and alkylated with a crosslinking agent selected from acrylamide and glycidol are new compounds.

During the alkylation of a crosslinked polyamino-polyamide polymer with acrylamide of the formula $CH_2=CH-CONH_2$, the latter condenses on the primary and/or secondary amine groups thus providing chains of the formula

glycidol under the same conditions provides chains of the formula $-N-CH_2-CHOH-CH_2OH$.

Unless otherwise indicated, all parts and percentages are by weight. The following examples are provided to illustrate the present invention.

EXAMPLE 1

Polycondensation of adipic acid and diethylene-triamine

The structure of the polymer obtained can be characterized by repeating units of the formula

876 g (6 mols) of adipic acid are added, with stirring and in a nitrogen atmosphere, over the course of 15 minutes, to 619 g (6 mols) of diethylene-triamine. The reaction mixture is then heated at 145°–150° C., at which temperature condensation water is noted. Refluxing is maintained for 45 minutes and then the water is removed by distillation at ambient or atmospheric pressure for 2 hours and then under reduced pressure (15 mm Hg) for 1 hour. The heating temperature increases gradually to 170° C.

The product thus obtained is cast when hot. After cooling, it is in the form of a hard, brittle and transparent yellow-green colored resin which dissolves completely in water.

EXAMPLE Ia

Crosslinking of the polymer prepared according to Example I, using epichlorohydrin 9 g of epichlorohydrin are added, with stirring, to 200 g of resin, prepared according to the process described in Example I, dissolved in 800 g of water. The mixture is heated to 90° C. and then 1.8 g of epichlorohydrin are added in very small portions and at intervals of 5 to 10 minutes until a viscosity greater than 50 centipoises at 65° C. is obtained.

The solution is then diluted immediately until its solids content is 10%, by adding 1,098 g of water.

The apparent viscosity, measured after 24 hours and at 25° C. is 31 centipoises at a rate of shear of 26.3 seconds $^{-1}$.

The amount of crosslinking agent used is 11 mols of epichlorohydrin per 100 amine groups.

EXAMPLE Ib

Crosslinking of the polymer prepared according to Example I, using methylene bisacrylamide 7 g of methylene bisacrylamide are added, at ambient temperature and with stirring, to 70 g of the polymer prepared according to the process described in Example I and dissolved in 280 g of water. The mixture is then heated to 80°–90° C. After heating for 1 hour, a large increase in the viscosity is observed. The mixture is then diluted until its solids content is 10% by adding 413 g of water.

A clear solution is obtained with an apparent viscosity of 32 centipoises, measured after 24 hours, at 25° C., and under a rate of shear of 26.3 seconds $^{-1}$.

The amount of crosslinking agent used is 12.1 mols of methylene bisacrylamide per 100 amine groups of the polyamino-polyamide.

EXAMPLE Ic

Crosslinking of the polymer prepared according to Example I, using N,N'-bis-epoxy-propyl-piperazine 1.50 g of N,N'-bis-epoxy-propyl-piperazine are added, at ambient temperature and with stirring, to 20 g of polymer prepared according to the process described in Example I and dissolved in 80 g of water. The resulting mixture is then heated to 70°–80° C. After heating for 15 minutes, the mixture is diluted immediately until its solids content is 10%, by adding 113.5 g of water.

A clear solution is obtained exhibiting a viscosity of 32 centipoises measured after 24 hours, at 25° C., and under a rate of shear of 26.3 seconds $^{-1}$. The amount of crosslinking agent used is 7.3 mols of N,N'-bis-epoxypropyl-piperazine per 100 amine groups of the polyamino-polyamide.

EXAMPLE Id

Crosslinking of the polymer prepared according to Example I, using divinyl-sulphone 1.7 g of divinyl-sulphone are added dropwise, at ambient temperature, to 20 g of polymer prepared according to Example I and dissolved in 80 g of water, until gelling starts. The mixture is then diluted rapidly with 100 ml of water.

The apparent viscosity of the resulting 10% strength solution, measured after 24 hours, at 25° C. and at a rate of shear of 26.3 seconds $^{-1}$, is 27 centipoises.

The amount of crosslinking agent used is 13.9 mols of divinyl-sulphone per 100 amine groups of the polyamino-polyamide.

EXAMPLE II

Polycondensation of adipic acid and a mixture of diethylene-triamine and piperazine The structure of the polymer prepared can be represented by the two units below, distributed statistically in the proportions of 2:1.

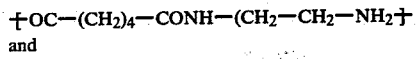
and
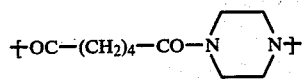

A mixture of 438 g (3 mols) of adipic acid and 86 g (1 mol) of piperazine is heated, with stirring, and in a nitrogen atmosphere, for 2 hours at 120°–135° C. 206 g (2 mols) of diethylene-triamine are then added, at this temperature and over the course of 90 minutes. The water formed is distilled for 1 hour at 140°–170° C. at atmospheric pressure, and then for 1 hour at 170°–175° C. under 15 mm Hg.

The product thus obtained is in the form of a yellow-green colored, transparent, brittle, hard resin.

EXAMPLE IIa

Crosslinking of the polymer prepared according to Example II, using epichlorohydrin.

9 g of epichlorohydrin are added, with stirring, at ambient temperature, to 200 g of resin, prepared according to Example II and dissolved in 800 g of water. The mixture is then heated to 90° C. and a further 1.1 g of epichlorohydrin are added in small portions at 5 or 10 minute intervals, until a viscosity of 50 centipoises is reached.

The solution is then diluted rapidly with 1,091 g of water in order to obtain a concentration of 10% of the crosslinked polymer.

The solution thus obtained is clear and its viscosity, measured after 24 hours, at 25° C., and at a rate of shear of 26.3 seconds $^{-1}$, is 52 centipoises.

The amount of crosslinking agent used is 13.2 mols of epichlorohydrin per 100 amine groups of the polyaminopolyamide.

EXAMPLE III

Polycondensation of adipic acid and triethylene-tetraamine

The makeup of the polymer prepared in this example can be represented by repeating units of the formula

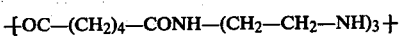

292 g (2 mols) of adipic acid are added in small portions and with stirring, under a nitrogen atmosphere, over the course of 20 minutes, to 292 g (2 mols) of triethylene-tetraamine. The mixture is then heated under full reflux at 145° C. for 1 hour. The water formed is removed by distillation at atmospheric pressure for 3 hours and under a reduced pressure of 15 mm of mercury for 1 hour, while gradually raising the temperature to 170°–175° C.

A yellow-brown colored transparent resin is thus obtained. A 10% strength solution of the polymer exhibits a viscosity, at 25° C., of less than 2 centipoises.

EXAMPLE IIIa

Crosslinking of the polymer prepared according to Example III, using epichlorohydrin 1.8 g of epichlorohydrin are added, rapidly and with stirring, to 200 g of a 20% strength aqueous solution of polymer prepared according to the process described in Example III, and the mixture is heated at 90°–95° C. for 30 minutes. 0.4 g of epichlorohydrin is then added, at the same temperature, very slowly, until a viscosity of more than 50 centipoises, measured at 65° C., is reached.

The solution is then diluted immediately until its solids content is 10%, by adding 220 g of water. The solution obtained is clear. Its viscosity at 25° C. and at a rate of shear of 26.3 seconds $^{-1}$ is 24 centipoises. The total amount of epichlorohydrin added is 0.0242 mol, which corresponds to 7.8 mols of crosslinking agent per 100 amine groups of the polyamino-polyamide.

EXAMPLE IIIb

Crosslinking of the polymer prepared according to Example III, using methylene bisacrylamide.

0.8 g of methylene bisacrylamide is added to 100 g of a 20% strength aqueous solution of polymer prepared according to the process described in Example III. The mixture is then heated at 70°–80° C. for 25 minutes. A soft gel is then obtained which is diluted immediately until its solids content is 10%, by adding 108 g of water. The solution obtained is clear. Its viscosity, measured after 24 hours, at 25° C. and at a rate of shear of 26.3 seconds $^{-1}$, is 43 centipoises.

The amount of methylene bisacrylamide added is equivalent to 3.4 mols of crosslinking agent per 100 amine groups of the polyamino-polyamide.

EXAMPLE IV

Polycondensation of the product resulting from the reaction of 2 mols of methyl itaconate and 1 mol of ethylene-diamine with diethylene-triamine The structure of the polymer prepared in this example can be represented by repeating units of the formula

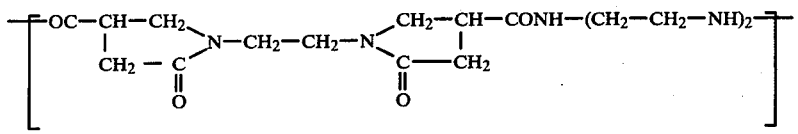

Step 1

118 g (1.95 mols) of ethylene-diamine are added, over the course of one hour, with stirring and under a nitrogen atmosphere, to 620 g (3.9 mols) of methyl itaconate, while maintaining the temperature at 30° C.

After the mixture has been left overnight at ambient temperature, it is heated to 80° C. in order to remove the methanol, first at atmospheric pressure and then under a reduced pressure of 15 mm Hg. The appearance of a precipitate is then noted. The reaction mixture is taken up in 500 ml of benzene and the methanol-benzene azeotrope is distilled.

The mixture is concentrated and the residue is taken up in acetone. N,N'-ethylene-bis-{2-[4'-(methyl-carboxylate)]pyrrolidone}, in the form of a white powder with a melting point of 141°–142° C. and a saponification index of 6.35 milli-equivalents/gram, is thus obtained in an 82% yield.

Step 2

65.5 g (0.63 mol) of diethylene-triamine are added, at ambient temperature, to 198 g (0.63 mol) of the diester prepared in Step 1 above and the methanol formed is distilled by heating at 120°–130° C., first at atmospheric pressure for 90 minutes and then under a reduced pressure of 15 mm Hg for 30 minutes.

A yellow-green colored, brittle, hard, transparent resin, which is perfectly soluble in water, is thus obtained.

EXAMPLE IVa

Crosslinking of the polymer prepared according to Example IV, using epichlorohydrin 13 g of epichlorohydrin are added, with stirring, at ambient temperature, to 200 g of the polymer of Example IV dissolved in 800 g of water. The mixture is heated to 90° C. and a further 2 g of epichlorohydrin are added, in small portions, at 5 or 10 minute intervals, until gelling starts. The mixture is then diluted rapidly with 1,135 g of cold water in order to bring the solids content of the solution to 10%.

A clear solution is thus obtained, the viscosity of which, measured after 24 hours, at 25° C. and at a rate of shear of 26.3 seconds $^{-1}$, is 49 centipoises.

The amount of epichlorohydrin used corresponds to 22 mols per 100 amine groups of the polyamino-polyamide.

EXAMPLE IVb

Crosslinking of the polymer prepared according to Example IV, using methylene bisacrylamide 1.5 g of methylene bisacrylamide are added, at ambient temperature and with stirring, to 50 g of polymer prepared in Example IV and dissolved in 200 g of water. The mixture is then heated to 85°–90° C. The said crosslinking agent is then added gradually until a viscosity of more than 50 centipoises at 65° C. is reached. The concentration of the mixture is then brought back to a 10% solids content, by adding 285 g of water.

A clear solution with a viscosity of 54 centipoises at 25° C. and at a speed gradient of 26.3 seconds $^{-1}$ is obtained.

The amount of methylene bisacrylamide added is 3.9 g and corresponds to 16 mols per 100 amine groups of the polyamino-polyamide.

EXAMPLE V

Polycondensation of a mixture of 2 mols of methyl acrylate and 1 mol of ethylene-diamine with diethylene-triamine The structure of the polymer prepared in this example can be represented by repeating units of the formula

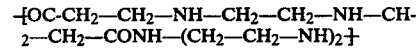

689 g (8 mols) of methyl acrylate are added, over the course of 2 hours, at a temperature of between 10° and 20° C., with stirring and under a nitrogen atmosphere, to 240 g (4 mols) of ethylene-diamine. After stirring for 1 hour at ambient temperature, 413 g (4 mols) of diethylene-triamine are added. The methanol formed is then distilled by heating at 120°–140° C. for 2 hours at atmospheric pressure and for 2 hours under a reduced pressure of 15 mm Hg.

A yellow-orange colored transparent resin is thus obtained which, in the form of a solution with a 10% solids content, has a viscosity of less than 2 centipoises.

EXAMPLE Va

Crosslinking of the polymer prepared according to Example V, using epichlorohydrin 45 g of epichlorohydrin are added, with stirring, at ambient temperature, to 200 g of polymer prepared according to the process of Example V and dissolved in 800 g of water. The mixture is heated gradually to 90° C. and then 11 g of epichlorohydrin are added, in small portions, at 5 or 10 minute intervals, until gelling starts. The concentration is then diluted rapidly to a 10% solids content, by adding 1,500 g of cold water.

A clear solution is thus obtained with a viscosity of 25 centipoises, measured after 24 hours, at 25° C. and at a rate of shear of 26.3 seconds $^{-1}$.

EXAMPLE VI

Polycondensation of a mixture of 2 mols of methyl methacrylate and 1 mol of ethylene-diamine with diethylene-triamine The structure of the polymer prepared in this example can be represented by repeating units of the formula:

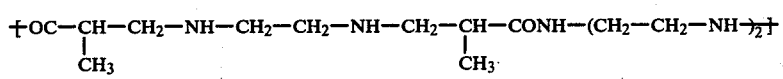

600 g of methyl methacrylate (6 mols) are added, at ambient temperature, to 180 g (3 mols) of ethylene-diamine. The mixture is left to stand for 3 days and is then heated to 80° C. for 3 hours. 309 g of diethylene-triamine (3 mols) are then added and the whole is heated at 120°–125° C. for 4 hours at atmospheric pressure and for 90 minutes under a reduced pressure of 15 mm Hg. The polycondensate thus obtained is in the form of a green-bronze colored resin.

EXAMPLE VIa

Crosslinking of the polymer prepared according to Example VI, using methylene bisacrylamide 27.3 g of methylene bisacrylamide are added, at ambient temperature and with stirring, to 84.6 g of polymer prepared according to the process described in Example VI and dissolved in 338.4 g of water. The mixture is then heated at 85°–90° C. for 15 minutes, after which it is diluted immediately until it has a solids content of 10%, by adding 669 g of water. A clear solution with a viscosity of 53 centipoises at 25° C. and a rate of shear of 26.3 seconds $^{-1}$ is obtained.

The amount of crosslinking agent added corresponds to 21.4 mols per 100 amine groups of the polyamino-polyamide.

EXAMPLE VII

Alkylation of the crosslinked polymer of Example Ia with propane sultone

To 3000 g of a 10% aqueous solution of the crosslinked polyamino-polyamide prepared in accordance with Example Ia, having a base index of 0.45 meq/g (1 g of polymer includes $0.45 \times 10^{-3}$ amine groups), there are added, with agitation and under a nitrogen atmosphere, 113.5 g (0.93 mol) of propane sultone. The resulting mixture is then heated to 60° C. for 4 hours, after which the reaction mixture is rapidly diluted with 1020 grams of water to restore the concentration of the polymer to 10%. The solution thus obtained is yellow and exhibits at 25° C. a viscosity of 12.6 centipoises.

EXAMPLE VIII

Alkylation of the crosslinked polymer of Example Ia with sodium chloroacetate.

To 2000 g of a 10% aqueous solution of the crosslinked polyamino-polyamide prepared in accordance with Example Ia, there are added with agitation and at ambient temperature, 70 g (0.6 mol) of sodium chloroacetate. The resulting mixture is then heated to 90° C. for 10 hours after which 270 g of water are added to restore the concentration of the polymer to 10%. There is thus obtained a clear pale yellow solution having a viscosity at 25° C. of 21 centipoises.

EXAMPLE IX

Alkylation of the crosslinked polymer of Example Ia with glycidol

To 1000 g of a 10% aqueous solution of the crosslinked polyamino-polyamide prepared in accordance with Example Ia, there are added over a two hour period with agitation and at ambient temperature, 27 g (0.36 mol) of glycidol. Agitation is continued for 5 hours and thereafter the reaction mixture is diluted with 265 g of water to restore the concentration of the polymer to 10%. There is obtained a clear, lightly colored solution having a viscosity, measured at 25° C., of 13.8 centipoises.

EXAMPLE X

Alkylation of the crosslinked polymer of Example Ia with acrylamide

To 1000 g of a 10% aqueous solution of the crosslinked polyamino-polyamide prepared in accordance with Example Ia, there are added at ambient temperature in the presence of a trace amount of sodium nitrite, 20 g (0.28 mol) of acrylamide. The resulting reaction mixture is then heated for 10 hours at 60° C. 180 g of water are then added to the reaction mixture, thus providing a clear solution containing 10% of the polymer and exhibiting a viscosity of 11.2 centipoises at 25° C.

EXAMPLE A 1

Anionic shampoo

| | |
|---|---|
| Triethanolamine lauryl sulphate | 15 g |
| Diethanolamides of copra fatty acids | 3 g |
| Polymer prepared according to Example Ia | 1.5 g |
| Water, q.s.p. | 100 g |
| pH = 7 | |

Approximately 10 cm³ of this solution are applied to a head of hair which has been moistened beforehand. The head of hair is massaged lightly. The hair is rinsed with water and a second application is effected. The head of hair is massaged vigorously in order to produce a large amount of foam which is left in contact with the hair for about a minute to ensure that the polymer is fixed to the hair. The head of hair is then rinsed.

It is found that the wet hair can be combed out very easily (the comb slips readily through the hair), the hair is very soft, supple and easy to handle, and can be set in waves very easily. After drying and when the dry hair is being set, it is also found that the head of hair can be combed out easily. The hair is full of life and easy to manage.

EXAMPLE A 2

Anionic shampoo

| | |
|---|---|
| Modified alkanolamide disodium sulphosuccinate semi-ester (sold commercially under the tradename "Monomate DHL 50") | 15 g |
| Sodium lauryl-ether-sulphate, condensed with 2.2 mols of | |

EXAMPLE A 3

Anionic shampoo

| | |
|---|---|
| Sodium lauryl-ether-sulphate condensed with 2.2 mols of ethylene oxide | 12 g |
| Diethanolamides of copra fatty acids | 4 g |
| Polymer according to Example Va | 1.5 g |
| Quaternary vinylpyrrolidone copolymers with a molecular weight of the order of 1,000,000, sold commercially under the tradename "GAFQUAT 755" | 0.3 g |
| Water, q.s.p. | 100 g |
| pH = 7.5 | |

*(continued from previous page)*

| | |
|---|---|
| ethylene oxide | 15 g |
| Polymer prepared according to Example Ia | 1 g |
| Water, q.s.p. | 100 g |
| pH = 7.8 | |

EXAMPLE A 4

Anionic shampoo

| | |
|---|---|
| Sodium myristyl-ether-sulphate, condensed with 2.5 mols of ethylene oxide | 5 g |
| Sodium lauryl-ether-sulphate, condensed with 2.2 mols of ethylene oxide | 1 g |
| Polymer according to Example IVa | 1 g |
| Water, q.s.p. | 100 g |
| pH = 8 | |

EXAMPLE A 5

Anionic shampoo

| | |
|---|---|
| Triethanolamine lauryl suphate | 10 g |
| Monoethanolamides of copra fatty acids | 1.5 g |
| Hydrolysate of proteins derived from collagen containing 80% of active materials, sold commercially under the tradename "HYDROPO 220" | 5 g |
| Polymer according to Example IIa | 2 g |
| Water, q.s.p. | 100 g |
| pH = 4 | |

The effect of the shampoos A 2 to A 4 is similar to that of the shampoo A 1. Shampoo A 5 also improves the condition of damaged hair by making the fibers stronger and the hair harder.

EXAMPLE A 6

Non-ionic shampoo

| | |
|---|---|
| R—CHOH—CH$_2$—O$+$CH$_2$—CHOH—CH$_2$—O$\frac{1}{3.5}$H wherein R = mixture of nonyl to dodecyl | 2.5 g |
| Polymer according to Example Ia | 2.5 g |
| Lactic acid, q.s.p. | pH=5 |
| Water, q.s.p. | 100 g |

EXAMPLE A 7

Non-ionic shampoo

| | |
|---|---|
| R—CHOH—CH$_2$—O$+$CH$_2$—CHOH—CH$_2$—O$\frac{1}{3.5}$H | 12 g |
| Dimethyl-hydroxymethyl-cetyl ammonium chloride | 1.5 g |
| Polymer prepared according to Example Ia | 1.5 g |
| Quaternary vinylpyrrolidone copolymers with a molecular weight of the order of 1,000,000 sold commerically under the tradename "GAFQUAT 755" | 0.2 g |
| Lactic acid, q.s.p. | pH 3 |
| Water, q.s.p. | 100 g |

EXAMPLE A 8

Non-ionic shampoo

| | |
|---|---|
| R—CHOH—CH$_2$—O$+$CH$_2$—CHOH—CH$_2$—O$\frac{1}{3.5}$H wherein R = mixture of nonyl to dodecyl | 5 g |
| Dimethyl-hydroxyethyl-cetyl-ammonium chloride | 1 g |
| C$_{12}$H$_{25}$—O$+$CH$_2$—CH—O$\frac{1}{4}$H $\quad$ \| $\quad$ CH$_2$OH | 5 g |
| Polymer of Example Va | 3 g |
| Lactic acid, q.s.p. | pH 5 |
| Water, q.s.p. | 100 g |

EXAMPLE A 9

Non-ionic shampoo

| | |
|---|---|
| Lauryl alcohol oxyethylenated with 12 mols of ethylene oxide | 7 g |
| Lauryl diethanolamide | 3 g |
| Polymer according to Example Ia | 0.5 g |
| Polymer according to Example IIa | 0.8 g |
| Lactic acid, q.s.p. | pH 4.5 |
| Water, q.s.p. | 100 g |

EXAMPLE A 10

Non-ionic shampoo

| | |
|---|---|
| Lauryl alcohol oxyethylenated with 12 mols of ethylene oxide | 6 g |
| C$_{12}$H$_{25}$O$+$CH$_2$—CH—O$\frac{1}{4}$H $\quad$ \| $\quad$ CH$_2$OH | 4 g |
| Lauryl diethanolamide | 1.5 g |
| Polymer according to Example IV a | 2 g |
| Lactic acid, q.s.p. | pH 3 |
| Water, q.s.p. | 100 g |

The non-ionic shampoos of Examples A6–A10 can be applied in the same way as the anionic shampoos of Examples A1–A5. It is found that wet hair and dry hair can be combed out very easily, with excellent results, and the hair retains suppleness and great lightness. The head of hair has bulk and can be set in waves easily.

EXAMPLE A 11

Wavesetting reinforcer

The following lotion is prepared:

| | |
|---|---|
| Vinyl acetate/crotonic acid copolymer, 90/10, MW = 10,000 | 2.5 g |
| Polymer according to Example Ia | 0.3 g |
| 2-amino-2-methyl-1,3-propane-diol, q.s.p. | pH 7 |
| Ethanol, q.s.p. 50° strength | |
| Dyestuff | 0.1 g |
| Perfume | 0.2 g |
| Water, q.s.p. | 100 ml |

EXAMPLE A 12

Wavesetting reinforcer for greasy hair
The following lotion is prepared:

| | |
|---|---|
| Polymer according to Example Ia | 0.3 g |
| Vinyl acetate/crotonic acid copolymer, 90/10, MW = 50,000 | 2.5 g |
| Vinylpyrrolidone/vinyl acetate copolymer, 60/40, Viscosity = 3.3 cps at 25° C. in 5% ethanol solution | 0.5 g |
| 2-amino-2-methyl-propanediol, q.s.p. | pH 7 |
| Ethanol, q.s.p. 50° strength | |
| Dye | 0.01 g |
| Perfume | 0.2 g |
| S-carboxymethylcysteine | 0.7 g |
| Water, q.s.p. | 100 ml |

The lotions of Examples A11 and A12 can be applied to wet hair which is towelled dry after shampooing and before being wound up in order to set it in waves.

It is found that wet hair can be combed out easily. After the hair has been wound up in order to set it in waves, it is found that the hair has more life, is softer and is slightly more glossy. The set stays in for a considerably longer period.

EXAMPLE A 13

Lotion for "brushing" (shaping)
The following lotion is prepared:

| | |
|---|---|
| Polymer according to Example Ia | 0.5 g |
| Ethanol, q.s.p. 50° strength | |
| Dye | 0.01 g |
| Perfume | 0.2 g |
| Water, q.s.p. | 100 ml |

This lotion is applied to wet hair which has been towelled dry after shampooing. The head of hair is shaped by means of a brush while drying the hair by means of a hand-held drier.

It is found that the brush passes through the hair very easily and that the set stays in for a long time. It is also found that the hair is glossier and softer.

EXAMPLE A 14

Rinse (rinsed lotion) for fine soft hair
The following lotion is prepared:

| | |
|---|---|
| Cetyl-stearyl alcohol, 30/70% oxyethylenated to the extent of 33%, sold commercially under the tradename "Sipol Wax AO" | 1.5 g |
| Dimethyl-distearyl-ammonium chloride, sold commercially under the tradename "ARQUAD 2HT 75" R—CHOH—CH$_2$—O$+$CH$_2$—CHOH—CH$_2$—O$+_{3.5}$H | 1.5 g |
| R = mixture of nonyl to dodecyl | 1 g |
| Polymer according to Example IIa | 2 g |
| Quaternary vinylpyrrolidone copolymers with a molecular weight of the order of 1,000,000, sold commercially under the tradename "GAFQUAT 755" | 0.5 g |
| Hydroxyethyl-cellulose | 0.9 g |
| Maleic acid, q.s.p. | pH 8 |
| Water, q.s.p. | 100 g |

This lotion is applied to wet hair which has been towelled dry after shampoiing, the lotion is left in place for 5 minutes, and then the hair is rinsed.

It is found that wet hair can be combed out very easily. After the hair has been set in waves and dried, it is full of life, easy to manage and glossy.

EXAMPLE A 15

Setting lotion
The following lotion is prepared:

| | |
|---|---|
| Polymer according to Example Va | 0.5 g |
| Silicone oil | 0.1 g |
| Hydroxyethyl-cellulose | 0.2 g |
| Ethanol | 50 ml |
| Perfume | 0.2 g |
| Water, q.s.p. | 100 ml |

This lotion, for men, is applied to wet hair. The hair is set and then dried. It is found that the hair is full of life and slightly harder and stays in place perfectly.

EXAMPLE A 16

Setting gel

| | |
|---|---|
| Polymer according to Example Ia | 1 g |
| Hydroxyethyl-cellulose | 2 g |
| Silicone oil | 0.5 g |
| Ethanol | 40 ml |
| Perfume | 0.02 g |
| Water, q.s.p. | 100 g |

When a small amount of this gel is applied to dry hair, it ensures that the set stays in well, while making the hair glossy.

EXAMPLE A 17

Structuring lotion, with no rinsing

| | |
|---|---|
| Dimethylol-ethylene-thiourea of the formula $$\begin{array}{c} \phantom{CH_2-N}\diagup CH_2OH \\ CH_2-N \\ \phantom{CH_2-N}\diagdown \\ \phantom{aaa}\diagup CS \\ CH_2-N \\ \phantom{CH_2-N}\diagdown CH_2OH \end{array}$$ | 0.5 g |
| Polymer according to Example Ia | 0.5 g |
| Phosphoric acid, q.s.p. | pH 3 |
| Water, q.s.p. | 100 ml |

This lotion is applied to hair which has been washed and towelled dry after shampooing, and before setting it in waves. It is found that, when wet, the hair can be combed out easily and that it feels silky.

After being set in waves and dried, the hair is glossy and full of life; it possesses body and bulk and is soft to the touch.

EXAMPLE A 18

A similar result is obtained by replacing in the lotion of Example A 17 the polymer prepared according to Example Ia by the polymer prepared according to Example IIa.

EXAMPLE A 19

Structuring lotion, applied with rinsing

| | |
|---|---|
| Dimethylol-ethylene-thiourea, of the formula 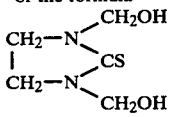 | 1 g |
| Polymer according to Example Ia | 1 g |
| Phosphoric acid, q.s.p. | pH 3 |
| Water, q.s.p. | 100 ml |

This lotion is applied to clean wet hair. It is left in contact with the hair for 10 minutes after which the hair is rinsed. The thus treated hair feels soft and can be combed out easily.

After the hair has been set in waves and dried, the comb passes easily through the hair which is glossy, full of life and bulky.

EXAMPLE A 20

An equally good result is obtained when, in the lotion of Example A19 the polymer according to Example Ia is replaced by the polymer according to Example IIa.

EXAMPLES A 21–A 22

Wavesetting lotion for hair which has been rendered sensitive

A 21: An aqueous solution of the compound prepared in Example Id, containing 1% of active material and 0.5% NaCl adjusted to pH 7 by means of citric acid, is prepared.

It is applied to bleached hair. The hair is set in waves and dried.

The hair is hardened and full of life; it feels silky and is easy to comb out.

A 22: An aqueous solution of the compound prepared in Example Ic, containing 1% of active material and 1.5% NH4Cl and adjusted to pH 5 by means of lactic acid, is prepared. It is applied to bleached hair. The hair is set in waves and dried. The hair is hardened. It is elastic and glossy. It feels silky and is easy to comb out.

EXAMPLE A 23

Treatment lotion, applied with rinsing 25 ml of the following solution are applied to clean wet hair:

| | |
|---|---|
| Polymer according to Example Ib | 1.5 g |
| Citric acid, q.s.p. pH 5 | |
| Water, q.s.p. | 100 g |

The solution is left in contact with the hair for 5 minutes after which the hair is rinsed. The hair feels soft and can be combed out easily. The hair is then set in waves and dried. The dry hair can be combed out easily. It is glossy and full of life.

EXAMPLE A 24

The same result is obtained by replacing 1.5 g of polymer according to Example Ib in the lotion of Example A 23 by 1 g of the polymer according to Example IIIa.

EXAMPLE A 25

Structuring lotion, applied without rinsing

| | |
|---|---|
| Dimethylol-ethylene-thiourea, of the formula 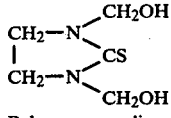 | 0.6 g |
| Polymer according to Example IIIb | 0.5 g |
| Phosphoric acid, q.s.p. | pH 3 |
| Water, q.s.p. | 100 g |

The mixture is applied to hair which has been washed and towelled dry, before setting it in waves. The hair can be combed out easily and feels silky. It is then set in waves and dried.

The hair is glossy, full of life, elastic and bulky. It feels silky and is easy to comb out.

EXAMPLE A 26

The same result is obtained if the polymer according to Example IIIb in the lotion of Example A 25 is replaced by the polymer according to Example IVb.

EXAMPLE A 27

Structuring lotion, applied with rinsing

| | |
|---|---|
| Dimethylol-ethylene-thiourea, of the formula 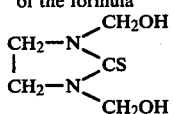 | 1.5 g |
| Polymer according to Example VIa | 1 g |
| Hydrochloric acid, q.s.p. | pH 3 |
| Water, q.s.p. | 100 g |

The mixture is applied to hair which has been washed and towelled dry. It is left in contact with the hair for 10 minutes after which the hair is rinsed. The hair is easy to comb out and feels soft and silky. It is set in waves and dried under a hood.

The dry hair can be combed out easily; it is glossy, full of life, elastic and bulky.

EXAMPLE A 28

Anionic shampoo

| | |
|---|---|
| Monoethanolamine lauryl sulphate | 10 g |
| Monoethanolamides of copra fatty acids | 1.5 g |
| Polymer according to Example Ic | 1 g |
| Lactic acid, q.s.p. | pH 7.2 |
| Water, q.s.p. | 100 g |

EXAMPLE A 29

Anionic shampoo

| Sodium lauryl-ether-sulphate oxyethylenated with 2.2 mols of ethylene oxide | 6 g |
|---|---|
| Triethanolamine lauryl sulphate | 6 g |
| Diethanolamides of copra fatty acids | 3 g |
| Polymer according to Example IIIa | 1.5 g |
| Lactic acid, q.s.p. | pH 7.6 |
| Water, q.s.p. | 100 g |

EXAMPLE A 30

Anionic shampoo

Same composition as the shampoo of Example A 29, except that the polymer according to Example IIIa is replaced by the polymer according to Example IIIb in essentially equivalent amounts.

EXAMPLE A 31

Anionic shampoo

| Sodium myristyl-ether-sulphate oxyethylenated with 2.5 mols of ethylene oxide | 6 g |
|---|---|
| Monoethanolamine lauryl-ether-sulphate, oxyethylenated with 2 mols of ethylene oxide | 9 g |
| Diethanolamides of copra fatty acids | 3.5 g |
| Hydrolysate of proteins derived from collagen, containing 80% of active materials, sold under the tradename of "Hydropo 220" | 3 g |
| Polymer according to Example IVb | 1 g |
| Lactic acid, q.s.p. | pH 7.5 |
| Water, q.s.p. | 100 g |

EXAMPLE A 32

Anionic shampoo

Same composition as the shampoo of Example A 31 except that the polymer according to Example IVb is replaced by the polymer according to Example VIa in essentially equivalent amounts.

The effect of the shampoo of Examples A 28 to A 30 is similar to that of the shampoo of Example A 1. The shampoos of Examples A 31 and A 32 also improve the condition of damaged hair, making the fibers stronger and the hair harder.

Example A 33

Non-ionic shampoo

| $C_{12}H_{25}O\text{---}[C_2H_3O(CH_2OH)]_{\overline{n}}\text{---}H$ wherein n represents an average statistical value of approximately 4 | 6 g |
|---|---|
| Lauryl alcohol oxyethylenated with 12 mols of ethylene oxide | 6 g |
| Carboxylic acid derivative of the imidazole of the formula $C_{11}H_{23}C\overset{\displaystyle OH}{\underset{\displaystyle \underset{N}{\parallel}}{\text{---}}}N\overset{\displaystyle CH_2\text{---}COONa}{\underset{\displaystyle CH_2\text{---}CH_2\text{---}O\text{---}CH_2\text{---}COONa}{\text{---}}}$ | 4 g |
| Polymer according to Example IIIb | 1 g |
| Lactic acid, q.s.p. | pH 5 |
| Water, q.s.p. | 100 g |

EXAMPLE A 34

Same composition as the shampoo of Example A 33, except that the polymer IIIb is replaced by the polymer Ic in essentially equivalent amounts.

EXAMPLE A 35

Same composition as the shampoo A 33, except that the polymer IIIb is replaced by the polymer IIIa in essentially equivalent amounts.

EXAMPLE A 36

Non-ionic shampoo

| Lauryl alcohol oxyethylenated with 12 mols of ethylene oxide | 10 g |
|---|---|
| Monoethanolamides of copra fatty acids | 1.5 g |
| Lauryl-dimethyl-amine oxide | 3 g |
| Polymer according to Example VIa | 0.5 g |
| Lactic acid, q.s.p. | pH 3.3 |
| Water, q.s.p. | 100 g |

EXAMPLE A 37

Same composition as the shampoo A 36, except that the polymer according to Example VIa is replaced by the polymer according to Example IVb in essentially equivalent amounts.

EXAMPLE A 38

| $C_{12}H_{25}O\text{---}[C_2H_3O(CH_2OH)]_{\overline{n}}\text{---}H$ wherein n represents an average statistical value of approximately 4 | 5 g |
|---|---|
| $R\text{---}CHOH\text{---}CH_2\text{---}O\text{---}[CH_2\text{---}CHOH\text{---}CH_2\text{---}O]_{\overline{n}}H$ wherein R = mixture of $C_9$-$C_{12}$ alkyl radicals and n represents an average statistical value of approximately 3.5 | 10 g |
| Polymer according to Example IIIb | 1.5 g |
| Lactic acid, q.s.p. | pH 5 |
| Water, q.s.p. | 100 g |

EXAMPLE A 39

Same composition as the shampoo of Example A 38, except that the polymer according to Example IIIb is replaced by the polymer according to Example IVb in essentially equivalent amounts.

The effect of the shampoos according to Examples A 33-A 39 is similar to that of the shampoos according to Examples A 6-A 10.

EXAMPLE A 40

Structuring lotion without rinsing

| Dimethylolethylene thiourea of the formula $\begin{array}{c}CH_2\text{---}N\overset{\displaystyle CH_2OH}{\underset{\displaystyle \phantom{CH_2OH}}{\diagdown}}\\ |\phantom{CH_2\text{---}N}\phantom{xxx}CS\\ CH_2\text{---}N\underset{\displaystyle CH_2OH}{\diagup}\end{array}$ | 0.5 g |
|---|---|
| Polymer of Example VII | 0.6 g |
| Phosphoric acid, q.s.p. | pH 3 |
| Water, q.s.p. | 100 cc |

This lotion is applied to hair washed and dried after shampooing and before setting. When wet, the hair is easily combed out and has a silky touch. After setting and drying, the hair is shiny and lively, has body and bulk and is soft to the touch.

EXAMPLE A 41

Lotion to increase the bulk of sensitized hair, applied with rinsing

| | |
|---|---|
| Calcium acetate | 2 g |
| Polymer of Example IX | 2 g |
| Phosphoric acid, q.s.p. | pH 8 |
| Water, q.s.p. | 100 cc |

This lotion is applied to wet clean hair. The hair has a soft touch and combs out easily. After setting and drying, the comb passes easily through the hair which is shiny, lively and bulky.

EXAMPLE A 42

Structuring lotion, applied with rinsing

| | |
|---|---|
| Dimethylolethylene thiourea of the formula 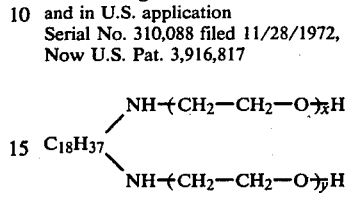 | 1 g |
| Polymer of Example VII | 0.5 g |
| Polymer of Example VIII | 0.4 g |
| Phosphoric acid, q.s.p. | pH 3 |
| Water, q.s.p. | 100 cc |

This lotion is applied to clean wet hair and is left in contact therewith for 10 minutes, after which the hair is then rinsed. The hair has a soft touch and combs out easily. After setting and drying, the comb passes easily through the hair which is shiny, lively and bulky.

EXAMPLE A 43

Non-ionic shampoo

| | |
|---|---|
| R—CHOH—CH$_2$—O—[CH$_2$—CHOH—CH$_2$—O$-]_{3.5}$H wherein R = C$_9$–C$_{12}$ alkyl | 15 g |
| Polymer of Example Ia | 1.5 g |
| NaCl | 1 g |
| Lactic acid, q.s.p. | pH = 3 |
| Water, q.s.p. | 100 ml |

When applied to sensitized hair, this clear shampoo composition produces an abundant and soft foam. It significantly improves the ease with which the hair is combed out and after drying the hair is lively, light and shiny.

EXAMPLE A 44

Non-ionic shampoo for sensitized hair

| | |
|---|---|
| R—CHOH—CH$_2$—O—[CH$_2$—CHOH—CH$_2$—O$-]_{3.5}$H wherein R = C$_9$ to C$_{12}$ alkyl | 17 g |
| Polymer of Example Ia | 0.8 g |
| Polymer comprising repeating units of the formula 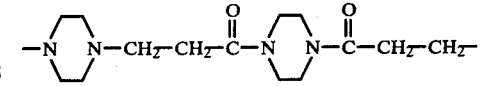 and prepare by the condensation of piperazine and piperazine bis-acrylamide, as described in Luxembourg Patent No. 64371 and in U.S. application Serial No. 310,088 filed 11/28/1972, Now U.S. Pat. 3,916,817 $C_{18}H_{37}$—N(NH—(CH$_2$—CH$_2$—O$)_x$H)(NH—(CH$_2$—CH$_2$—O$)_y$H) wherein x + y = 5 | 1.5 g |
| NH$_4$Cl | 1.2 g |
| Lactic acid, q.s.p. | pH = 3.5 |
| Water, q.s.p. | 100 ml |

When applied to sensitized hair, this clear shampoo composition produces an abundant and soft foam which is easily eliminated by rinsing the hair. The thus treated hair is combed out without difficulty and after drying the hair possesses bulk and liveliness, while remaining soft and easy to style.

EXAMPLE A 45

Non-ionic shampoo for sensitized hair

| | |
|---|---|
| C$_{12}$H$_{25}$—O—[C$_2$H$_3$O(CH$_2$OH)$-]_8$H | 17 g |
| Polymer of Example IVa | 1.8 g |
| Lauryl diethanolamide | 3 g |
| NaCl | 0.8 g |
| Lactic acid, q.s.p. | pH = 5 |
| Water, q.s.p. | 100 ml |

When applied to sensitized hair, this clear shampoo produces an abundant and agreeable foam and facilitates combing out of the wet hair. After drying the hair is soft, shiny and very lively while remaining controlled.

EXAMPLE A 46

Wavesetting reinforcer for oil or greasy hair

| | |
|---|---|
| Copolymer of vinyl acetate/crotonic acid, 90/10, MW = 25,000 | 2.5 g |
| Copolymer of polyvinylpyrrolidone/vinyl acetate, 60/40 - viscosity of 5% solution in ethanol at 25° C. = 3.3 cps | 0.5 g |
| Polymer of Example VII | 0.3 g |
| S-carboxymethyl cysteine | 0.7 g |
| Triethanolamine, q.s.p. | pH = 8.6 |
| Ethyl alcohol | 10 ml |
| Water, q.s.p. | 100 ml |

This lotion is applied to hair towelled dry after shampooing and before rolling up on wave setting rollers. The wet hair is easily combed out. After rolling up on the rollers and drying, the hair is lively, more soft and clearly more shiny. The hold of the set is considerably prolonged.

EXAMPLE A 47

Wavesetting reinforcer for oily or greasy hair

| | |
|---|---|
| Copolymer of vinyl acetate/crotonic acid, 90/10, MW = 70,000 | 2.5 g |
| Copolymer of vinylpyrrolidone/vinyl acetate, 60/40, viscosity of 5% solution in ethanol at 25° C. = 4 cps. | 0.5 g |
| Polymer of Example VII | 0.3 g |
| Triethanolamine, q.s.p. | pH = 7 |
| Ethyl alcohol | 10 ml |
| Water, q.s.p. | 100 ml |

This lotion is applied to hair towelled dry after shampooing and before rolling up on wave setting rollers. The wet hair is easily combed out. After rolling up on the rollers and drying, the hair is more lively, more soft and clearly more shiny. The hold of the set is considerably prolonged.

EXAMPLE A 48

Wavesetting reinforcer for oily or greasy hair

| | |
|---|---|
| Copolymer of vinyl acetate/crotonic acid, 90/10, MW = 50,000 | 2.5 g |
| Copolymer of vinylpyrrolidone/ vinyl acetate, 60/40, viscosity of a 5% solution in ethanol at 25° C. = 3.5 cps | 0.5 g |
| Polymer of Example IX | 0.3 g |
| Triethanolamine, q.s.p. | pH = 7 |
| Ethyl alcohol | 10 ml |
| Water, q.s.p. | 100 ml |

This lotion is applied to hair towelled dry after shampooing and before rolling up on wave setting rollers. The wet hair is easily combed out. After rolling up the hair on wave set rollers and drying, the hair is more lively, more soft and clearly more shiny. The hold of the set is considerably prolonged.

EXAMPLE A 49

Wavesetting reinforcer for oily or greasy hair

| | |
|---|---|
| Copolymer of vinyl acetate/crotonic acid, 90/10, MW = 50,000, neutralized with triethanolamine | 2.5 g |
| Copolymer of vinylpyrrolidone/ vinyl acetate, 60/40, viscosity of a 5% solution in ethanol at 25° C. = 3.7 cps | 0.5 g |
| Polymer of Example Ia | 0.5 g |
| Dimethyl hydroxymethyl cetyl ammonium chloride | 0.1 g |
| NaCl | 0.5 g |
| Hydrochloric acid, q.s.p. | pH = 8 |
| Ethyl alcohol | 50 ml |
| Water, q.s.p. | 100 ml |

This lotion is applied to hair towelled dry after shampooing. The hair is then styled with a brush while drying the hair with a hand held drier. The brush passes easily through the hair and the hold of the resulting coiffure is prolonged. The hair is shiny and soft.

EXAMPLE A 50

Structuring lotion without rinsing
Dimethylolethylene thiourea of the formula:

| | |
|---|---|
| $\begin{array}{c} CH_2-N \\ | \\ CH_2-N \end{array} \begin{array}{c} CH_2OH \\ \diagdown \\ CS \\ \diagup \\ CH_2OH \end{array}$ | 0.5 g |
| Polymer of Example X | 0.6 g |
| Phosphoric acid, q.s.p. | pH = 3 |
| Water, q.s.p. | 100 ml |

This lotion is applied to hair towelled dry after shampooing but before setting. The wet hair is easily combed out and has a silky touch. After setting and drying, the hair is shiny and lively, has body and bulk and is soft to the touch.

EXAMPLE A 51

Rinse lotion for fine, soft hair

| | |
|---|---|
| Petrolatum oil | 7.5 g |
| Dimethyl distearyl ammonium chloride | 1 g |
| R—O—(—C$_2$H$_3$O(CH$_2$OH)—)$_{16}$—H wherein R = C$_{16}$-C$_{18}$ alkyl | 3.75 g |
| C$_{12}$H$_{25}$O—(—C$_2$H$_3$O(CH$_2$OH)—)$_{14}$—H | 3.75 g |
| Polymer of Example IX | 2 g |
| Quaternary copolymers of vinylpyrrolidone having a MW in the order of 1,000,000, sold under the tradename "GAFQUAT 755" | 2.5 g |
| Citric acid, q.s.p. | pH = 3 |
| Water, q.s.p. | 100 g |

This lotion is applied to hair towelled dry after shampooing and is left in contact therewith for 5 minutes. The hair is then rinsed and is easily combed out. After setting and drying, the hair is lively, easy to style and shiny.

EXAMPLE A 52

Anionic shampoo

| | |
|---|---|
| Triethanolamine lauryl sulfate (40% active material) | 30 g |
| Diethanolamides of the fatty acids of coprah | 1.5 g |
| Polymer of Example Ia - 100% active material | 1 g |
| Polymer having repeating units of the formula —(—Y—CH$_2$—CHOH—CH$_2$—)— where Y represents $-N\diagup\diagdown N-$ or $\begin{array}{c}-N-\\|\\CH_2\\|\\CH_2-O-CH_2O\end{array}$, these two Y values being statistically distributed | 0.5 g |
| Water, distilled, q.s.p. | 100 g |
| pH = 7 | |

About 10 cc of this clear solution are applied to previously wetted hair which is then massaged lightly. Thereafter the hair is rinsed with water and a second application of the above composition is effected. The hair is then massaged vigorously to obtain an abundant foam which is left in contact with the hair for about a minute to assure fixing of the polymer on the hair. The hair is then rinsed and is easily combed out. The hair is very soft, supple and manageable and the setting of the same is achieved with great ease. After drying and during the styling of the dry hair, it is easily combed out and is lively and controlled.

EXAMPLE A 53

Cationic shampoo

| | |
|---|---|
| Tetradecyltrimethylammonium | 75 g |
| Lauryl alcohol polyoxyethylenated with 12 moles of ethylene oxide | 50 g |
| Polymer of Example Ia | 5 g |
| Polymer having repeating units of the formula $+Y-CH_2-CHOH-CH_2+$ as defined in Example A 52 | 0.5 g |
| Lactic acid, q.s.p. | pH = 5 to 5.5 |
| Water, distilled, q.s.p. | 1000 g |

This clear solution is applied to dyed hair. After massaging, the hair is rinsed with water and a second application to the hair of the above composition is effected. The hair is then rinsed. The wet hair is easily combed out and is very soft, supple and manageable. The setting of the hair is achieved with great ease. After drying, and during the styling of the hair, the hair is easily combed and is lively and controlled.

What is claimed is:

1. A cosmetic composition for treatment of hair comprising a solution in a solvent selected from the group consisting of water and a hydroalcoholic solution of a water-soluble crosslinked polymer selected from the group consisting of
   (A) a polyamino-polyamide which is the polycondensate of methyl itaconate and a mixture of ethylene diamine and diethylene triamine and the said polyamino-polyamide is crosslinked with a crosslinking agent selected from the group consisting of epichlorohydrin, methylene bisacrylamide, N,N'-bis epoxy propyl piperazine and divinyl sulfone; and
   (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone; said crosslinked polymer being soluble in water in amounts of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition.

2. A cosmetic composition for treatment of the hair comprising a solution in a solvent selected from the group consisting of water and a hydroalcoholic solution of a water-soluble crosslinked polymer selected from the group consisting of
   (A) a polyamino-polyamide which is the polycondensate of methyl acrylate and a mixture of ethylene diamine and diethylene triamine and the said polyamino-polyamide is crosslinked with a crosslinking agent selected from the group consisting of epichlorohydrin, methylene bisacrylamide, N,N'-bis epoxy propyl piperazine and divinyl sulfone; and
   (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone; said crosslinked polymer being soluble in water in amounts of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition.

3. A cosmetic composition for treatment of the hair comprising a solution in a solvent selected from the group consisting of water and a hydroalcoholic solution of a water-soluble crosslinked polymer selected from the group consisting of
   (A) a polyamino-polyamide which is the polycondensate of methyl methacrylate and a mixture of ethylene diamine and diethylene triamine and the said polyamino-polyamide is crosslinked with a crosslinking agent selected from the group consisting of epichlorohydrin, methylene bis acrylamide, N,N'-bis epoxy propyl piperazine and divinyl sulfone; and
   (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone; said crosslinked polymer being soluble in water in amounts of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition.

4. A cosmetic composition for treatment of the hair comprising a solution in a solvent selected from the group consisting of water and a hydroalcoholic solution of a water-soluble crosslinked polymer, said polymer being a polyamino-polyamide comprising a polycondensate of (a) an acidic compound selected from the group consisting of (i) an organic dicarboxylic acid selected from the group consisting of a saturated aliphatic dicarboxylic acid, having from 6 to 10 carbon atoms and an aromatic dicarboxylic acid, (ii) an ethylenically unsaturated carboxylic acid selected from the group consisting of acrylic acid, methacrylic acid and itaconic acid, (iii) an ester of said acids of (i) and (ii), and (iv) mixtures of (i), (ii) and (iii) and (b) a polyamine selected from the group consisting of (1) diethylene triamine, (2) dipropylene triamine, (3) triethylene tetramine and (4) a mixture with at least one of (1), (2) and (3) with a member selected from the group consisting of ethylene diamine, hexamethylene diamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide, said crosslinked polyamino-polyamide being alkylated with an alkylating agent selected from the group consisting of glycidol, ethylene oxide, propylene oxide, acrylamide, acrylic acid, chloroacetic acid, propane sulfone, and butane sulfone; said crosslinked polymer being soluble in water in amounts of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1-5 percent by weight of said composition.

5. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) an acidic compound selected from the group consisting of (i) an organic dicarboxylic acid selected from the group consisting of a saturated aliphatic dicarboxylic acid having from 6 to 10 carbon atoms and an aromatic dicarboxylic acid, (ii) an ethylenically unsaturated carboxylic acid selected from the group consisting of acrylic acid, methacrylic acid and itaconic acid, (iii) an ester of said acids of (i) and (ii), (iv) mixtures of (i), (ii) and (iii) and (v) the intermediate product of addition of one mole of ethylene diamine and two moles of a methyl ester of (ii) obtained at a temperature between 5°-80° C., and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0-20 mole percent hexamethylene diamine, (2) 0-40 mole percent ethylene diamine and (3) 0-40 mole percent piperazine wherein the polycondensate is formed at a temperature of 80°-250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025-0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1-5 percent by weight of said composition, and an effective amount of a surface active agent selected from the group consisting of nonionic, anionic, cationic, amphoteric and zwitterionic surface active agents.

6. The composition of claim 5 wherein said polyamino-polyamide is crosslinked with 0.025 up to about 0.1 mole of said crosslinking agent per amine group in said polyamino-polyamide.

7. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) adipic acid and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0-20 mole percent hexamethylene diamine, (2) 0-40 mole percent ethylene diamine and (3) 0-40 mole percent piperazine, wherein said polycondensate is formed at a temperature of 80° to 250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025-0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1-5 percent by weight of said composition, and an effective amount of a surface active agent selected from the group consisting of nonionic, anionic, cationic, amphoteric and zwitterionic surface active agents, wherein said polyamino-polyamide is crosslinked with 0.025 up to about 0.1 mole of said crosslinking agent per amine group in said polyamino-polyamide.

8. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) an acidic compound selected from the group consisting of (i) an organic dicarboxylic acid selected from the group consisting of a saturated aliphatic dicarboxylic acid having from 6 to 10 carbon atoms and an aromatic dicarboxylic acid, (ii) an ethylenically unsaturated carboxylic acid selected from the group consisting of acrylic acid, methacrylic acid and itaconic acid, (iii) an ester of said acids of (i) and (ii), (iv) mixtures of (i), (ii) and (iii) and (v) the intermediate product of addition of one mole of ethylene diamine and two moles of a methyl ester of (ii) obtained at a temperature between 5°-80° C., and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at a temperature of 80°–250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and an effective amount of a cosmetic resin.

9. The composition of claim 8 wherein said polyamino-polyamide is crosslinked with 0.25 up to about 0.1 mole of said crosslinking agent per amine group in said polyamino-polyamide.

10. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) adipic acid and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at 80°–25° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and an effective amount of a cosmetic resin, wherein said polyamino-polyamide is crosslinked with 0.025 up to about 0.1 mole of said crosslinking agent per amine group in said polyamino-polyamide.

11. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) an acidic compound selected from the group consisting of (i) an organic dicarboxylic acid selected from the group consisting of a saturated aliphatic dicarboxylic acid having from 6 to 10 carbon atoms and an aromatic dicarboxylic acid, (ii) an ethylenically unsaturated carboxylic acid selected from the group consisting of acrylic acid, methacrylic acid and itaconic acid, (iii) an ester of said acids of (i) and (ii), (iv) mixtures of (i), (ii) and (iii) and (v) the intermediate product of addition of one mole of ethylene diamine and two moles of a methyl ester of (ii) obtained at a temperature between 5°–80° C., and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at a temperature of 80°–250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and an effective amount of dimethylol ethylene thiourea to reinforce the keratinic chain of the hair.

12. The composition of claim 11 wherein said polyamino-polyamide is crosslinked with 0.025 up to about 0.1 of said crosslinking agent per amine group in said polyamino-polyamide.

13. A cosmetic composition for treatment of the hair comprising a solution in a solvent selected from the group consisting of water and a hydroalcoholic solution of a water-soluble crosslinked polymer selected from the group consisting of
(A) a polyamino-polyamide which is the polycondensate of (a) adipic acid and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at 80° to 250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and
(B) a crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and
an effective amount of dimethylol ethylene thiourea to reinforce the keratinic chain of the hair,
wherein said polyamino-polyamide is crosslinked with 0.025 up to about 0.1 mole of said cross-linking agent per amine group in said polyamino-polyamide.

14. A cosmetic composition for treatment of the hair comprising a solution in a solvent selected from the group consisting of water and a hydroalcoholic solution of a water-soluble crosslinked polymer selected from the group consisting of
(A) a polyamino-polyamide which is the polycondensate of (a) an acidic compound selected from the group consisting of (i) an organic dicarboxylic acid selected from the group consisting of a saturated aliphatic dicarboxylic acid having from 6 to 10 carbon atoms and an aromatic dicarboxylic acid, (ii) an ethylenically unsaturated carboxylic acid selected from the group consisting of acrylic acid, methacrylic acid and itaconic acid, (iii) an ester of said acids of (i) and (ii), (iv) mixtures of (i), (ii) and (iii) and (v) the intermediate product of addition of one mole of ethylene diamine and two moles of a methyl ester of (ii) obtained at a temperature between 5°–80° C., and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at a temperature of 80°–250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025°–0.35 mole per amine group in said polyamino-polyamide; and
(B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and
an effective amount of a water-soluble electrolyte so as to reduce the tendency of said polyamino-polyamide to fix durably on the hair.

15. The composition of claim 14 wherein said polyamino-polyamide is crosslinked with 0.025 up to about 0.1 mole of said crosslinking agent per amine group in said polyamino-polyamide.

16. A cosmetic composition for treatment of the hair comprising a solution in a solvent selected from the group consisting of water and a hydroalcoholic solution of a water-soluble crosslinked polymer selected from the group consisting of
(A) a polyamino-polyamide which is the polycondensate of (a) adipic acid and (b) a polyamide selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at 80°–250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and 10 weight percent aqueous solution of said crosslinked polymer having a viscosity greater than 3 centipoises at 25° C., said water soluble crosslinked polymer being present in an amount of about 0.1–5 percent by weight of said composition, and an effective amount of a water-soluble electrolyte so as to reduce the tendency of said polyamino-polyamide to fix durably on the hair, wherein said polyamino-polyamide is crosslinked with 0.025 up to about 0.1 mole of said crosslinking agent per amine group of said polyamino-polyamide.

17. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) an acidic compound selected from the group consisting of (i) an organic dicarboxylic acid selected from the group consisting of a saturated aliphatic dicarboxylic acid having from 6 to 10 carbon atoms and an aromatic dicarboxylic acid, (ii) an ethylenically unsaturated carboyxlic acid selected from the group consisting of acrylic acid, methacrylic acid and itaconic acid, (iii) an ester of said acids of (i) and (ii), (iv) mixtures of (i), (ii) and (iii) and (v) the intermediate product of addition of one mole of ethylene diamine and two moles of a methyl ester of (ii) obtained at a temperature of 5°–80° C., and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at a temperature of 80°–250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and a mixture consisting essentially of an effective amount of each of hydroxyethyl cellulose and silicone oil to provide a hair setting composition.

18. The composition of claim 17 wherein said polyamino-polyamide is crosslinked with 0.025 up to about 0.1 mole of said crosslinking agent per amine group in said polyamino-polyamide.

19. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) adipic acid and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at 80° to 250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and a mixture consisting essentially of an effective amount of each of hydroxyethyl cellulose and silicone oil to provide a hair setting composition, wherein said polyamino-polyamide is crosslinked with 0.025 up to about 0.1 mole of said crosslinking agent per amine group in said polyamino-polyamide.

20. A cosmetic composition for treatment of the hair comprising a solution in a solvent selected from the group consisting of water and a hydroalcoholic solution of a water-soluble crosslinked polymer selected from the group consisting of (A) a polyamino-polyamide which is the polycondensate of (a) an acidic compound selected from the group consisting of (i) an organic dicarboxylic acid selected from the group consisting of a saturated aliphatic dicarboxylic acid having from 6 to 10 carbon atoms and an aromatic dicarboxylic acid, (ii) an ethylenically unsaturated carboxylic acid selected from the group consisting of acrylic acid, methacrylic acid and itaconic acid, (iii) an ester of said acids of (i) and (ii), (iv) mixtures of (i), (ii) and (iii) and (v) the intermediate product of addition of one mole of ethylene diamine and two moles of a methyl ester of (ii) obtained at a temperature between 5°–80° C., and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at a temperature of 80°–250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyaminopolyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition, and an effective amount of a member selected from the 3.oup consisting of an anionic, cationic, nonionic, amphoteric or zwitterionic surface active agent; a thickener; a preservative; and a cosmetic resin.

21. The composition of claim 20 wherein said polyamino-polyamide is crosslinked with 0.025 up to about 0.1 mole of said crosslinking agent per amine group in said polyamino-polyamide.

22. The composition of claim 21 wherein the polyamino-polyamide is a polycondensate of adipic acid and diethylene triamine and is crosslinked with epichlorohydrin in an amount of 0.025 to about 0.1 mole of epichlorohydrin per mole of amine of the polyaminopolyamide.

23. A process for conditioning the hair which comprises applying to living human hair an effective amount of a composition comprising a solution in a solvent selected from the group consisting of water and a hydroalcoholic solution of a water-soluble crosslinked polymer selected from the group consisting of (A) a polyamino-polyamide which is the polycondensate of (a) an acidic compound selected from the group consisting of (i) an organic dicarboxylic acid selected from the group consisting of a saturated aliphatic dicarboxylic acid having from 6 to 10 carbon atoms and an aromatic dicarboxylic acid, (ii) an ethylenically unsaturated carboxylic acid selected from the groups consisting of acrylic acid, methacrylic acid and itaconic acid, (iii) an ester of said acids of (i) an (ii), (iv) mixtures of (i), (ii) and (iii) and (v) the intermediate product of addition of one mole of ethylene diamine and two moles of a methyl ester of (ii) obtained at a temperature between 5°–80° C., and (b) a polyamine selected from the group consisting of (1) diethylene triamine, (2) dipropylene triamine, (3) triethylene tetramine and (4) a mixture of at least one of (1), (2) and (3) with a member selected from the group consisting of ethylene diamine, hexamethylenediamine and piperazine, said polyamine (b) being replaceable by a member selected from the group consisting of (1) 0–20 mole percent hexamethylene diamine, (2) 0–40 mole percent ethylene diamine and (3) 0–40 mole percent piperazine, wherein the polycondensate is formed at a temperature of 80°–250° C., said polyamino-polyamide being crosslinked with a crosslinking agent being selected from the group consisting of epichlorohydrin, diglycidyl ether, N,N'-bis-epoxypropyl piperazine, the dianhydride of butane tetracarboxylic acid, the dianhydride of pyromellitic acid, divinyl sulfone and methylene bisacrylamide, and being employed in an amount of 0.025–0.35 mole per amine group in said polyamino-polyamide; and (B) the crosslinked polymer of (A) alkylated with an alkylating agent selected from the group consisting of glycidol, ethylene oxide, propylene oxide, acrylamide, acrylic acid, chloracetic acid, sodium chloracetate, propane sultone and butane sultone, said crosslinked polymer being soluble in water in an amount of 10 weight percent thereof without essentially any gel formation and a 10 weight percent aqueous solution of said crosslinked polymer having a viscosity greater than 3 centipoises at 25° C., said water soluble crosslinked polymer being present in an amount of about 0.1–5 percent by weight of said composition.

24. The process of claim 23 wherein said polyamino-polyamide is crosslinked with 0.025 up to about 0.1 mole of said crosslinking agent per amine group in said polyamino-polyamide.

25. A process for conditioning the hair which comprises applying to living human hair an effective amount of a composition comprising a solution in a solvent selected from the group consisting of water and a hydroalcoholic solution of a water-soluble crosslinked polyamino-polyamide which is the polycondensate of adipic acid and diethylene triamine crosslined with epichlorohydrin, said crosslinked polyamino-polyamide being soluble in water in amounts of 10 weight percent thereof without essentially any gel formation and a 10 weight percent aqueous solution of said crosslinked polyamino-polyamide having a viscosity greater than 3 centipoises at 25° C., said water soluble crosslinked polyamino-polyamide being present in an amount of about 0.1–5 percent by weight of said composition.

* * * * *